US00RE37596E

(19) United States
(12) Reissued Patent
Bosslet et al.

(10) Patent Number: US RE37,596 E
(45) Date of Reissued Patent: Mar. 19, 2002

(54) MONOCLONAL ANTIBODIES AGAINST TUMOR-ASSOCIATED ANTIGENS, A PROCESS FOR THE PREPARATION THEREOF AND THE USE THEREOF

(75) Inventors: Klaus Bosslet, Berlin; Bernhard Auerbach; Helmut Peters, both of Marburg, all of (DE)

(73) Assignee: Dade Behring Marburg GmbH, Marburg (DE)

(21) Appl. No.: 09/333,987

(22) Filed: Jun. 16, 1999

Related U.S. Patent Documents

Reissue of:
(64) Patent No.: 5,639,622
Issued: Jun. 17, 1997
Appl. No.: 08/478,860
Filed: Jun. 7, 1995

U.S. Applications:

(63) Continuation of application No. 08/222,370, filed on Apr. 4, 1994, now abandoned, which is a continuation of application No. 07/658,393, filed on Feb. 20, 1991, now abandoned.

(30) Foreign Application Priority Data

Feb. 22, 1990 (DE) ..... 40 05 630

(51) Int. Cl.[7] ..... G01N 33/574; C12N 5/20
(52) U.S. Cl. ..... 435/7.23; 435/7.1; 435/344.1; 435/329; 435/325; 530/388.1; 530/388.15; 530/388.2; 530/388.85; 530/387.5
(58) Field of Search ..... 435/7.1, 7.23, 435/325, 344.1, 329; 530/388.1, 388.15, 388.2, 388.85, 387.5

(56) References Cited

U.S. PATENT DOCUMENTS 4,503,143 A * 3/1985 Gerber et al. ..... 435/7.1
5,284,931 A * 2/1994 Springer et al. ..... 424/85.8

FOREIGN PATENT DOCUMENTS

EP WO-0323802 A * 7/1989 ..... C12P/21/02

OTHER PUBLICATIONS

Schol et al., "MAb 123C3 identifying SCLC phenotype in lung tumors, recognizes mainly, but not exclusively, endocrine and neuron–supporting normal tissues," Int. J. Cancer 2(Supp):34–40 (1988).*
DeLey, et al. "Neuroendocrine and epithelial antigens in SCLC," Lung Cancer, 4:42–44 (1988).*
Udea et al., "Serological and Biochemical Analysis of four antigens associated with SCLC," Lung Cancer, 4:96–98. (1988).*
Hirohashi et al., "145KDa cell membrane Ag on SCLCs as a common target for several MAb raised against SCLCs," Lung Cancer, 4:103–104. (1988).*
Rosier et al., "Flow cytometry analysis of the reactivity on human blood leucocytes of a group of Mab reacting with SCLC and neural tissues," Lung Cancer, 4:58–61. (1988).*
Roitt, Encyclopedia of Immunology, 1992, Academic Press, London, U.K., pp. 1444–1445.*
S. Pahlman et al., "Purification and Characterization of Human Neuron–Specific Enolase: Radioimmunoassay Development," Tumour Biology, 5:127–139 (1984).*
A. Maier et al., "Expression of the Small Cell Carcinoma Antigens of Cluster–5 and Cluster 5–A in Primary Lung Tumours," Br. J. Cancer, 59:692–695 (1989).*
R. L. Souhami et al., "The First International Workshop on Small Cell Lung Cancer Antigens," Lung Cancer, 4:1–4 (1988).*
K. Patel et al., "Neural Cell Adhesion Molecule (NCAM) is the Antigen Recognized by Monoclonal Antibodies of Similar Specific in Small–Cell Lung Carcinoma and Neuroblastoma," Int. J. Cancer, 44:573–578 (1989).*
K. Patel et al., "Monoclonal Antibody UJ13A Recognizes the Neural Cell Adhesion Molecule (NCAM)," Int. J. Cancer, 44:1062–1068 (1989).*
J. Finne et al., "An IgG Monoclonal Antibody to Group B Memingococci Cross–Reacts with Developmentally Reguated Polysialic Acid Units of Glycoproteins in Neural and Extraneural Tissues," The Journal of Immunology, 0022–1767:4402–4407 (1987).*
J. Hayrinen et al., "Interaction of Meningococcal Group B Monoclonal Antibody and its Fab Fragment with α2–8–Linked Sialic Acid Polymers: Requirement of a Long Oligosaccharide Segment fro Binding, " Molecular Immunology, 26:523–529 (1989).*
P. T. Jones et al., "Replacing the Complementarity–Determining Regions in a Human Antibody With Those From a Mouse," Nature, 321:522–525 (1986).*
M. Verhoeyen et al., "Reshaping Human Antibodies: Grafting an Antilysozyme Activity," Science, 239:1534–1536 (1988).*
M. Shulman et al., "A Better Cell Line for Making Hybridomas Secreting Specific Antibodies," Science, 276:269–270 (1978).*
G. Kohler et al., "Continuous Cultures of Fused Cells Secreting Antibody of Predefined specificity," Nature, 256:495–497 (1975).*
J. L. Cordell et al., "Immunoenzymatic Labeling of Monoclonal Antibodies Using Immune Complexes of Alkaline Phosphatase and Monoclonal Anti–alkaline Phosphatase (APAAP Complexes), " The Journal of Histochemistry and Cytochemistry, 32:219–229 (1984).*

(List continued on next page.)

*Primary Examiner*—James Ketter
(74) *Attorney, Agent, or Firm*—Finnegan, Henderson, Farabow, Garrett and Dunner, L.L.P.

(57) ABSTRACT

The invention relates to monoclonal antibodies (MAbs) and fragments thereof which bind to defined tumor-associated antigens, principally of small cell lung carcinoma (SCLC), of melanoma, of neuroblastoma and other tumors of neuroectodermal origin, to hybridoma cell lines for the preparation thereof, and to the antigens which can be defined and/or isolated with the aid of these antibodies or antibody fragments. The antibodies, antibody fragments and antigens can be used as diagnostic, aid, active substance or active substance carrier.

19 Claims, 2 Drawing Sheets

OTHER PUBLICATIONS

P. L. Ey et al., "Isolation of Pure IgG.sub.1, IgG.sub.2b Immunoglobulins From Mouse Serum Using Protein A–Sepharose," Immunochemistry, 15:429–436 (1978).*

Kibbelaar, R. E., et al., "Expression of the Embryonal Neural Cell Adhesion Molecule N–Cam in Lung Carcinoma. Diagnostic usefulness of monoclonal antibody 735 for the distinction between small cell lung cancer and non–small cell lung cancer," *J. Pathol.* J. Finne et al., 159:23–28 (1989).

Watanabe, J. et al., "Monoclonal Antibody that Distinguishes Small–Cell Lung Cancer from Non–Small–Cell Lung Cancer," *Cancer Res.* 47:826–829 (Feb. 1, 1987).

Kitty Moolenaar, C., et al., "Expression of Neural Cell Adhesion Molecule–related Sialoglycoprotein in Small Cell Lung Cancer and Neuroblastoma Cell Lines H69 and CHP–212," *Cancer Res.* 50:1102–1106 (Feb 15, 1990).

Fuchs, B. B., et al., "Biochemical and Immunochemical Analysis of Gangliosides of Human Small Cell Lung Carcinoma: Production of Monoclonal Antibodies against a Unique Marker of Small Cell Lung Carcinoma, Ganglioside Fuc $GM_1$" *Biotechnology and Applied Biochemistry* 10: 273–286 (1988).

* cited by examiner

MONOCLONAL ANTIBODIES AGAINST TUMOR-ASSOCIATED ANTIGENS, A PROCESS FOR THE PREPARATION THEREOF AND THE USE THEREOF

Matter enclosed in heavy brackets [ ] appears in the original patent but forms no part of this reissue specification; matter printed in italics indicates the additions made by reissue.

This application is a continuation of application Ser. No. 08/222,370, filed Apr. 4, 1994, now abandoned, which is continuation of application Ser. No. 07/658,393 filed Feb. 20, 1991, now abandoned.

The invention relates to monoclonal antibodies (MAbs) and fragments thereof which bind to defined tumor-associated antigens, principally of small cell lung carcinoma (SCLC), of melanoma, of neuroblastoma and other tumors of neuroectodermal origin, to hybridoma cells for the preparation thereof, and to the antigens which can be defined and/or isolated with the aid of these antibodies or antibody fragments. The antibodies, antibody fragments and antigens can be used as diagnostic aid, active substance or active substance carrier.

The identification, characterization and therapy of tumors is one of the most important areas of diagnosis and therapy. Development in this area has made great advances owing to the possibility of producing monoclonal antibodies of high specificity. Particularly important in this connection has proven to be the identification of so-called tumor markers. By tumor markers are meant products of the tumor cell, for example tumor-associated antigens, but also substances formed by the healthy tissue as reaction of the body to the malignant growth. Examples of known tumor markers are CEA, AFP but also tumor antigens defined by monoclonal antibodies, such as, for example, CA 19-9 or CA 125.

The main area of use of tumor markers in in vitro diagnosis is in the therapy and monitoring the progress of tumor patients. Certain tumor markers can also be employed for differential diagnosis or for screening of risk groups.

A number of tests have already been carried out for the identification of small cell lung carcinoma (SCLC). Thus, for example, it is known that there is increased formation of neuron-specific enolase, an isoenzyme of enolase (EC 4.2.1.11), by malignant tumors of neuroectodermal origin, such as, for example, small cell bronchial carcinoma or neuroblastoma, and increased serum concentrations thereof occur in tumor patients.

However, it has emerged that false negative results are given by some of the patients suffering from the above-mentioned tumors. Furthermore, since red blood cells, but also platelets, contain relatively large amounts of NSE, it is the case that, owing to lysis thereof, falsely raised NSE serum or plasma levels and thus false positive values are measured (Pahlman et al., Tumor Biology 5: 127–139, 1984).

European Patent Application 0,323,802 discloses a monoclonal antibody against a cell surface antigen of lung carcinomas. However, MAIER et al. (Br. J. Cancer, 1989, 59, 692–695) disclose that the antibody SWA 20 used in EP 0,323,802 recognizes an epitope (cluster 5) which showed a moderately to strongly positive reaction only with 45% of tested SCLC samples.

It is therefore desirable to produce another specific tumor marker, which is independent of NSE, for neuroblastoma and small cell lung carcinoma.

Figure 1:
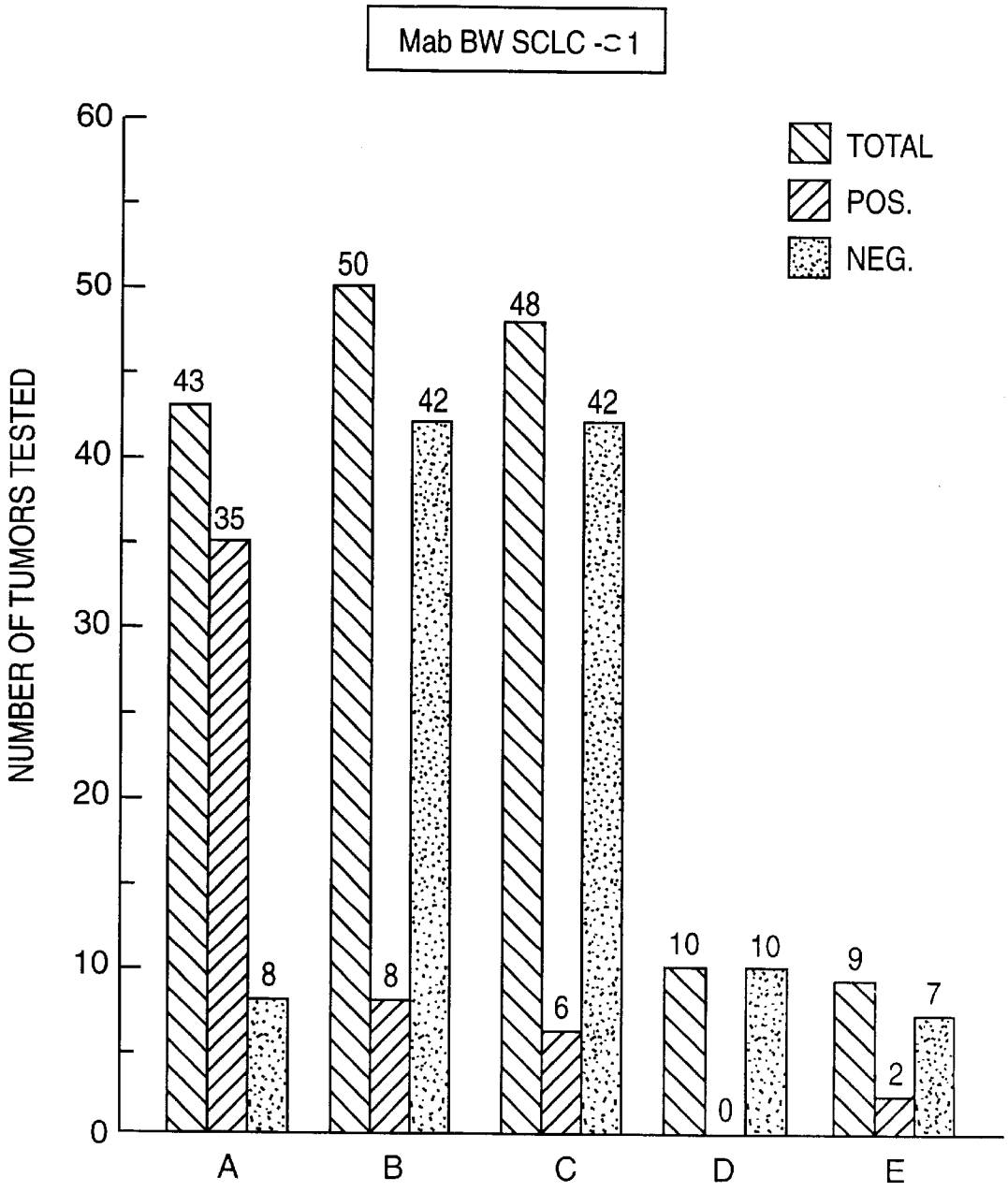
FIG. 1 shows the immunohistomchemical specificity of MAb BW SCLC-1 for human lung tumors. A: small cell carcinomas, D: undifferentiated carcinomas, B: adenocarcinomas, E: bronchiolo-alveolar carcinomas, and C: squamous cell carcinomas.

Monoclonal antibodies against a tumor-associated antigen are now proposed according to the invention, where the antigen originates from tumors principally belonging to the group of neuroectodermal tumors such as, for example, small cell lung carcinoma (SCLC), melanoma, neuroblastoma and from the culture supernatant from cell lines of these tumors, in particular antigens from SCLC cell lines which have a molecular weight of 170±10 kDa, 140±10 kDA, 105±10 kDA, 67±10 kDa and 50±10 kDA in the non-reducing SDS PAGE, or that the antigen originates from body fluids from tumor patients, especially antigens from the serum of SCLC patients which have molecular weights of 220–260 kDA and 160–200 kDA in the non-reducing SDS PAGE. These bands are detected with the MabBW SCLC-1 in the Westernblot and found in 5 of 5 SCLC tumor patients. No band was found for 2 of 4 normal sera, and very weak bands were found in the same position as in the tumor sera for 2.

Preferred monoclonal antibodies in this connection are those which bind to an antigen which is also bound by the reference antibodies MAb BW SCLC-1 and/or MAb BW SCLC-2.

Particularly preferred monoclonal antibodies in this connection are those which are produced by at least one of the hybridoma cell lines BW SCLC-1 and SCLC-2.

The invention furthermore relates to hybridoma cell lines which produce monoclonal antibodies according to the invention, with the hybridoma cell lines BW SCLC-1 and 2 being particularly preferred.

Monoclonal antibodies are defined within the scope of this invention to include antibody fragments such as, for example, Fab and $F(ab)_2$ and derivatives. The hybridoma cell lines BW SCLC-1 and 2 which produce the monoclonal antibodies MAb BW SCLC-1 and MAb BW SCLC-2 were deposited on Feb. 21, 1990, at the European Collection of Animal Cell Cultures (ECACC) under the numbers 90 022 110 and 90 022 109 respectively.

The invention furthermore relates to specific binding partners such as, for example, mono- or polyclonal antibodies, lectins and similar substances which are distinguished by being able to bind to the same epitopes as the reference antibodies. Reference antibodies within the scope of the invention are the MAbs BW SCLC-1 and SCLC-2.

Monoclonal antibodies can be prepared by processes known per se to those skilled in the art, preferably using for the immunization antigens from the supernatant of SCLC cell lines which have a molecular weight of 170±10 kDA, 140±10 KDa, 105±10, 67±10 kDA or 50±10 kDA in the non-reducing SDS PAGE. The invention also relates to antigens which can be bound by immunoadsorption to an antibody as claimed in claim 1.

Immunoadsorption is defined within the scope of the invention as isolation methods which are known per se to those skilled in the art and in which at least one purification step is based on an immunochemical reaction between the antibody as claimed in claim 1, preferably as claimed in claim 2, according to the invention. The removal of the Ab-Ag complex can, in this connection, be carried out in a manner known per se those skilled in the art, for example by binding the antibody to a solid phase.

The invention also relates to the use of an antigen according to the invention for generating an immune response in mammals, with humans being expressly included in this connection.

The invention also relates to the use of the antibodies and/or antigens according to the invention in diagnosis and/or therapy.

In diagnosis, antibodies are preferably employed in heterogeneous or homogeneous immunochemical determination methods known per se to those skilled in the art, and in the case of homogeneous methods particle-enhanced nephelometry or turbidimetry is preferred. In the case of heterogeneous immunoassays, the solid-phase-bound sandwich assay is preferred, in which case the solid phase is preferably a polystyrene tube, a latex particle, a magnetizable particle or a sheet-like solid phase. A diagnostic method for detecting a tumor-associated antigen is preferred, in which case an antibody according to the invention is employed as specific binding partner.

The antibodies and antigens according to the invention can also be employed in biosensors. Biosensors are known per se to those skilled in the art. A particularly preferred method is one in which a second specific binding partner is employed, such as, for example, an antibody, a lectin or a receptor.

Very particularly preferred in this connection is a method in which the second specific binding partner specifically recognizes sialic acid, polysialic acid or α-(2-8)-linked N-acetylneuraminic acid.

It is possible in this connection for one of the specific binding partners to carry a detectable label for detection and for quantification. These labels are known per se to those skilled in the art and can be, for example, a chromophore, a luminophore, a fluorophore, an enzyme, a radioactive isotope or a colored or else uncolored particle. A preferred method is one in which the unlabelled specific binding partner is coupled, by processes known per se to those skilled in the art, directly or indirectly, for example via another antibody or a biotinavidin bridge, to a solid phase.

Furthermore particularly preferred are the embodiments described in the examples.

The MAbs BW SCLC-1 and -2 can, because of their immunohistochemical binding to normal human tissue and tumors, be called SCLC cluster 1 MAbs (Souhami et al., LANCET, 8 Aug. 1987, 325–326). This cluster contains MAbs which optimally bind to small cell lung carcinomas. In addition, these MAbs bind to neural tissue, neuroblastomas and some melanomas.

Patel et al. (Int. J. Cancer 44: 573–578, 1989) have shown that these cluster 1 MAbs recognize N-CAM, in particular mainly the 140 and 180 kDa isoforms (Patel et al., Int. J. Cancer 44: 1062–1068, 1989). To date, no description has yet appeared of the active secretion of N-CAM and, in particular, the 160–180, 130–150, 95–115, 57–77 or 40–60 kDa (culture supernatant) and the 220–260 kDa and 160 to 200 kDa (serum) isoform by tumor cells, and thus the possibility of using it as tumor marker. Since N-CAM is detectable, inter alia, in the nerve, muscle, and kidney tissue (Roth et al., Proc. Natl. Acad. Sci. USA 85, 2999–3003, 1988; Roth et al., Virchows Archiv B 56, 95–102, 1988), it can be expected that there may also be changes in the N-CAM concentration in the body fluids of the patients in other pathological processes, especially affecting these tissues, so that N-CAM can also be used as diagnostic marker for these diseases.

Not only can the specificity of the MAbs BW SCLC-1 and -2 be used for an immunohistochemical differentiation of various tumor tissues and normal tissues, but, surprisingly, a combination of an anti-N-CAMMAb as solid-phase antibody which recognizes α-(2-8)-linked N-acetylneuraminic acid (Finne et al., J. Immunol. 138: 4402–4407, 1987; H ayrinen et al., Molecular Immunology 26: 523–529, 1989) with the MAbs BW SCLC-1 and -2 as conjugate antibodies has proven particularly suitable for developing a tumor marker immunoassay. This assay has been used to demonstrate that the antigens recognized in the serum or plasma of patients with SCLC and neuroblastoma are frequently present in a concentration which is distinctly higher than in the serum or plasma of healthy control subjects. It is possible to deduce from this that the sensitivity of the assay for the said tumors is good.

The antibodies BW SCLC-1 and -2 or the fragments thereof can also be radiolabelled by processes known to those skilled in the art in order to employ them for immunoscintigraphy or else for immunotherapy. In addition, these monoclonal antibodies might be employed as active substance carriers, for example for cytotoxins, and used for the therapy of malignant disease. The production of antibody constructs, for example by inserting the hypervariable regions into a human MAb framework, is also technically possible after analysis of the complete nucleotide sequence of the V genes of the MAbs BW SCLC-1 and -2 (Jones et al., Nature 321: 522–525, 1986; Verhoeyen et al., Science 239:1534–1536, 1988).

The antigens according to the invention can also be used for preparing an active vaccine, and suitable antibodies can be used for preparing a passive vaccine.

The examples which follow serve to illustrate the invention without restricting it in any way.

EXAMPLE 1

Generation of the monoclonal antibodies BW SCLC-1 and -2

The human small cell lung carcinoma cell lines GOT and MR 22 were used as immunogen. They were cultivated in vitro as suspension culture in basal medium (DMEM) to which 10% bovine serum is added. Balb/c mice were immunized with cells washed 3× in saline (PBS) in accordance with the following scheme:

| Day of injection | Cell count/ mouse | Route | Adjuvant | Cell type |
|---|---|---|---|---|
| 0 | $1.5 \times 10^7$ | S.C | CFA | MR 22 |
| 7 | $1 \times 10^7$ | S.C. | CFA | GOT |
| 14 | $1 \times 10^7$ | S.C. | IFA | MR22 |
| 21 | $1 \times 10^7$ | S.C. | IFA | GOT |
| 28 | $1 \times 10^7$ | S.C. | IFA | MR 22 |
| 32 | $2 \times 10^6$ | i.v. | PBS | GOT |
| 33 | $2 \times 10^6$ | i.v. | PBS | MR 22 |

(Abbreviations: CFA = complete Freund's adjuvant, IFA = incomplete Freund's adjuvant S.C. = subcutaneous i.v. = intravenous)

The spleens of the mice immunized in this way were removed on day 35 and fused in a ratio of 6:1 (spleen cells to myeloma cells) with the SP-2 myeloma cell line (Shulman et al., Nature 276: 269, 1978) by the technique described by Köhler and Milstein (Köhler and Milstein, Nature 256: 495, 1975).

The hybrids which grew in the period of 8–28 days were assayed by cytofluorometric analysis to find whether they secrete MAbs which bind to the GOT and the MR 22 SCLC cell lines. Positive hybrids were cloned 3× by the limited dilution technique, and the MAbs produced by these subclones were subjected to various immunological assay methods. Hybrids which, on the basis of these immunological assays, secrete particularly interesting MAbs were frozen in liquid nitrogen and deposited under the name BW SCLC-1 or BW SCLC-2 at the ECACC under the deposit No.90 022 109 or 90 022 110. The MAbs secreted by these hybrids are called MAb BW SCLC-1 or MAb BW SCLC-2.

EXAMPLE 2

Immunohistochemical characterization of the specificity of the Mab BW SCLC-1 and MAb BW SCLC-2

The APAAP technique (Cordell et al., J. Histochem. Cytochem. 32:219, 1984) was used to determine the expression of the epitopes which were recognized by both MAbs on cryopreserved normal human tissues and tumors. It emerged from this that the expression is confined to tumors of neuroectodermal origin, i.e. more than 80% of small cell lung carcinomas (FIG. 1), neuroblastomas and brain tumors were clearly positive (Tab. 1), as was a large proportion of the malenomas. Most other tumors not derived from the neuroectoderm were negative (see Tab. 1). The reactions of MAb BW SCLC-1 with cryopreserved normal human tissues are compiled in Tab. 2. The reaction pattern shown by MAb BW SCLC-2 was comparable. The only difference was more pronounced binding to bone marrow.

EXAMPLE 3

Characterization of the antigens and epitopes recognized by MAb BW SCLC-1 and MAb BW SCLC-2

The MAb BW SCLC-1 was purified by protein A affinity chromatography and just like the MAb735, which is directed against α-(2-8)-linked N-acetylneuraminic acid, coupled to CNBr-activated Sepharose (Ey et al., Immunochemistry 15: 429, 1978; Pharmacia Fine Chemicals, Affinity Chromatography, Principles and Methods, pages 15–18, 1979). Cell culture media in which the GOT cell line was cultivated were pumped over the CNBr-activated Sepharose column loaded with MAb BW SCLC-1, and the antigen material specifically bounded at pH 7 was eluted at pH 2.5. The resulting eluate was fractionated by SDS polyacrylamide gel electrophoresis (SDS PAGE) both under reducing and under non-reducing conditions, subsequently subjected by methods known to those skilled in the art either to a silver stain or transferred to nitrocellulose (Western blot) and examined immunochemically for the presence of antigens of MAb BW SCLC-1 or -2 and other MAbs of known specificity.

The following findings were made during this:

a) Both the antigen recognized by MAb BW SCLC-1 and that recognized by MAb BW SCLC-2 occur in the supernatants from epitope-positive small cell lung carcinoma cell lines.

b) The molecular weight of the antigens is 170±10 kDa, 140±10 kDa, 105±10 kDa, 67±10 kDa and 50±10 kDa in the non-reducing SDS PAGE. The width of the bands indicates glycoproteins. Under reducing conditions the antigens are no longer recognized by MAbs BW SCLC-1 and -2.

After immune staining of the Western blot with the MAb BW SCLC-1 it is possible to detect only the antigens with a molecular weight of 170±10 kDa, 140±10 kDa and 105±10 kDa.

c) After treatment of the antigens with Vibrio cholerae neuraminidase (0.1 U/ml for 12 h at 37° C.) and after treatment with $NaIO_4$ (1 mM; 1 h, 25° C.), both MAbs were still able to bind to the antigen. These findings indicate that the epitopes defined by MAbs BW SCLC-1 and -2 on the glycoprotein antigens are protein epitopes.

These findings are supported by the fact that the epitopes are destroyed by protease treatment (Pronase P; 0.1 mg/ml; 72 h; 37° C.).

d) Two MAbs against N-CAM (neural cell adhesion molecules) (Kibbelaar et al., Journal of Pathology, 159: 23–28, 1989) which were employed for comparison both showed binding to the 170±10 kDa, 140±10 kDa and 105±10 kDa antigens. MAb 735 is directed against α-(2-8)-linked N-acetylneuraminic acid. It is to be assumed that the smaller, preferentially stained glycoprotein band of 105±10 kDa is probably the smaller of the 3 isoforms of N-CAM which are detectable in relatively high concentrations besides the larger N-CAM isoforms is supernatants from small-cell lung carcinoma cell lines. The affinity constant of Mab BW-SCLC-1 was determined in a cell-binding assay on 3 different human glioma cell lines and is in the region of $1\times10^{10}M^{-1}$.

e) After affinity chromatography with the MAb BW SCLC-1 SDS PAGE under non-reducing conditions end the Western blot were used to detect in sera from SCLC tumor patients two antigens with a molecular weight of 70–80 end 90–120 kDe, these probably being isoforms of N-CAM. In addition, affinity chromatography with the MAb 735-sepharose was used to isolate from sera of SCLC patients antigens which, under non-reducing conditions in the SDS PAGE, have a molecular weight of 220–260 kDa and 160–220 kDa and which can be immunochemically stained with the MAb BW SCLC-1 in the Western blot. Antigens of this type were not desirable Dr in significantly lower amounts in the serum of healthy blood donors under the same experimental conditions.

Subsequently, a radioimmunoassay (RIA) was used to measure the binding of the MAb BW SCLC-1 labeled with I-125 to, in each case, 2 human melanoma cell and neuroblastoma cell lines cultivated in vitro. It was found that, at 37° C., the MAb bound very rapidly to epitopepositive cell lines (1–5 min) but was released again relatively rapidly (>10 min at 37° C.). At 4° C. the MAb remained bound to the tumor cells for a long time. This finding and the presence of the five previously mentioned glycoproteins (N-CAM isoforms) in supernatants from small cell lung carcinoma cell lines indicated active release of the antigens by tumors of neuroectodermal origin.

After biotinylation of MAbBW SCLC-1, it was additionally possible to show, by a double determinant assay, that the N-CAM glycoproteins carry at least 2 epitopes for this MAb. Competition studies with MAbBW SCLC-2 revealed that the 2 MAbs recognize different epitopes on the same antigen.

EXAMPLE 4

Immunoassay for determining the tumor-associated antigen in human body fluids Methods known to those skilled in the art were used to bind the MAb 735 by adsorption to the polystyrene surface of the wells of microtiter plates and to couple MAbs BW SCLC-1 and BW SCLC-2 covalently to the enzyme peroxidase. To determine the concentration of the tumor-associated antigen which is described hereinbefore, in each case 10 μl of sample material and 100 μl of sample buffer (OSND, Behringwerke) were pipetted into the wells of microtiter plates (NUNC) which were coated with MAb 735 and incubated at 37° C. for 2 hours.

Three washes with the diluted Enzygnost washing buffer (OSEW, BW) were followed by 100 μl of the MAb BW SCLC-1-POD or BW SCLC-2-POD conjugate being filled into each one of the wells. The subsequent two-hour incubation step at 37° C. was terminated by a cycle of three washes.

For the 3rd incubation step at room temperature, subsequently 100 μl of a buffer/substrate chromogen solution ($H_2O_2$/TMB; OUVG/OUVF, BW) were pipetted into each of the wells, and the enzyme reaction was stopped after 30 min with Enzygnost stop solution (OSFA, BW). The extinction of the samples at 450 nm was determined.

Figure 2:
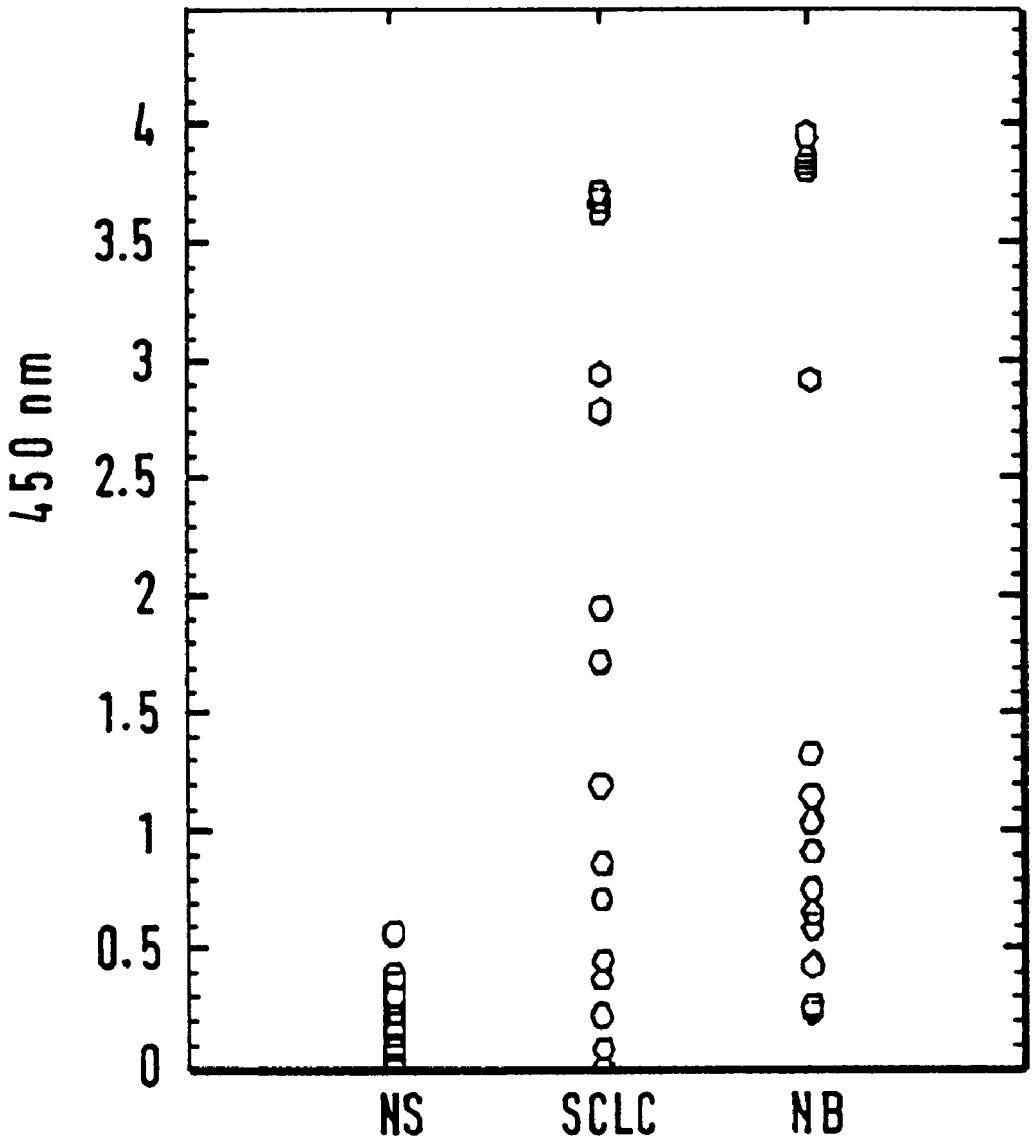
FIG. 2 shows the immunoassay for determining the tumor-associated antigen(s). NS: Serum samples from healthy blood donors (n=61); SCLC: serum samples from patients with a small cell lung carcinoma before therapy (n=22); NB: serum samples from patients with neuroblastoma (N=18).

Result: The extinctions determined using this immunoassay are at a level corresponding to the concentration of the tumor-associated antigen(s) in the samples. It emerged that the concentration of tumor-associated antigen(s) in the sera of patients with a small cell lung carcinoma or a neuroblastoma is often higher than in healthy blood donors (FIG. 2).

Higher antigen levels were observed in tumor sera with other assay combinations too (for example solid-phase antibody: MAbBW SCLC-1, conjugate: wheat germ agglutinin-POD=WGA-POD; solid-phase antibody: MAb BW SCLC-2, conjugate: MAb BW SCLC-1-POD). However, the difference between the serum or plasma samples from healthy people and those from patients with malignant tumors was not as pronounced as with the assay variants described hereinbefore.

TABLE 1

Immunohistochemical specificity of MAb BW SCLC-1 for cryopreserved human tumors

| Tumor type | Number of tumors: Total | Negative | Positive | Reaction type |
|---|---|---|---|---|
| Bronchial carcinomas | | | | |
| Small cell | 43 | 8 | 35 | TC +/+++MC |
| Large cell | 22 | 20 | 2 | STA (+)/+ |
| Squamous cell | 67 | 59 | 8 | FTA (+)/+ |
| Adenocarcinoma | 61 | 53 | 8 | weakly positive + |
| Ovary | 6 | 0 | 6 | CT(+)/+ |
| Breast | 12 | 6 | 6 | STC (+)/+MC. SCTF + |
| Stomach | 7 | 3 | 4 | TC (+)++ |
| Colon | 12 | 4 | 8 | STA+, MU, |
| Panchreas | 6 | 4 | 2 | SA+ |
| Kidney | 15 | 8 | 7 | TC (+)++, CT+/++ |
| Testes | 1 | 1 | 0 | |
| Bladder | 2 | 2 | 0 | |
| Prostate | 6 | 2 | 4 | SA + |
| Brain tumors | 13 | 0 | 13 | TC +++ MC |
| Neuroblastoma | 62 | 0 | 62 | muscle fibers ++, TC ++ M |
| Melanomas | 11 | 4 | 7 | STA +/++ |
| Ganglioneuroblastomas | 11 | 1 | 10 | |

TABLE 1-continued

Immunohistochemical specificity of MAb BW SCLC-1 for cryopreserved human tumors

| Tumor type | Number of tumors: Total | Negative | Positive | Reaction type |
|---|---|---|---|---|
| Ganglioneuromas | 6 | 6 | 0 | |
| Ewing's sacromas | 4 | 4 | 0 | |

Explanation of symbols:
TC = tumor cells, M = membrane, C = cytoplasm, STA = some tumor areas,
FTA = few tumor areas, CT = connective tissue, STC = some tumor cells, SCTF = some connective tissue fibers, MU = muscus, SA = some areas

TABLE 2

Immunohistochemical speciticity of MAb BW SCLC-1 for cryopreserved normal human tumors

| Tissue type | Number of tissues: Tested | Negative | Positive | Reaction type |
|---|---|---|---|---|
| Normal tissue: | | | | |
| Lung | 4 | 2 | 2 | (+) SC++ |
| Kidney | 3 | 0 | 3 | SV and CTF +/++ |
| Liver | 3 | 0 | 3 | CTF +,SV ducts +/++ |
| Stomach | 2 | 0 | 2 | CTF +/++ V ++ |
| Intestine | 3 | 0 | 3 | muscle (+V +,CTF and V ++ |
| Panchreas | 3 | 0 | 3 | islets + CTF and V ++ |
| Prostate | 2 | 0 | 2 | muscle +, homogenous + |
| Breast | 3 | 1 | 2 | epithelium ++, +/++ diff. |
| Brain | 9 | 0 | 9 | ++/+++ |
| Lymph node | 2 | 0 | 2 | SC+MC |
| Bone marrow | 5 | 3 | 2 | FC+MC |
| Spleen | 2 | 0 | 2 | (+),V(+V + |
| Testes | 1 | 0 | 1 | S duets (+V++ |
| Bladder | 1 | 0 | 1 | S muscle fibers +/++ |
| Nerves | 1 | 0 | 1 | nerve fiber +++ |
| Tonsils | 1 | 0 | 1 | SCTF+,S muscle fibers +, FC +/++ |
| Ovary | 1 | 0 | 1 | epethelium ++,SC CT ++ |
| Thymus | 1 | 0 | 1 | SC +, Hassal bodies ++ |
| Cytofluorometric analysis for peripheral blood cells | | | | |
| Lymphocytes | 2 | *2.8% | 0 | |
| Monocytes | 2 | *2.5% | 0 | |
| Granulocytes | 2 | *0.8% | 0 | |

TABLE 2-continued

Immunohistochemical speciticity of MAb BW SCLC-1 for cryopreserved normal human tumors

| Tissue type | Number of tissues: Tested | Negative | Positive | Reaction type |
|---|---|---|---|---|
| Erythrocytes | 2 | *0.2% | 0 | |
| Platelets | 2 | *0.5% | 0 | |

Explanation of symbols:
SC = some cells
SV = some vesssels.
CTF = connective tissue fibers
FC = few cells
S = some
M = membrane
C = cytoplasm
*proportion of fluorescent cells, below background.

We claim:

1. A hybridoma cell line which produces the monoclonal antibody BW SCLC-1 having the deposit number ECACC No. 90022110.

2. A monoclonal antibody (MAb) produced by the hybridoma cell line of claim 1.

3. An antibody which binds to the epitope recognized by the MAb of claim 2.

4. An antibody that has the same antigen binding [specifically] *specificity* as the MAb claimed in claim 2.

5. A method for determination of the antigen *recognized by the MAb* of claim 2, comprising the steps of:

a) incubating a sample of body fluid with a first antibody bound directly or indirectly to a solid phase, wherein said first antibody is selected from the group consisting of antibodies as claimed in claims 2, 3 or 4;

b) contacting any antigen bound to said solid phase with a second antibody recognizing sialic acid, polysialic acid or α-(2-8)-linked n-acetylneuraminic acid; and c) determining the amount of label from one of the antibodies bound via said antigen.

6. The method as claimed in claim 5 wherein said first antibody recognizes sialic acid, polysialic acid or α-(2-8)-linked n-acetylneuraminic acid, and wherein said second antibody is selected from the group consisting of antibodies as claimed in claims 2, 3, and 4.

*7. A heterogeneous or homogeneous method for the detection and determination of NCAM recognized by MAb BW SCLC-1, comprising the steps of:*

*a) incubating a sample of body fluid with a first specific binding partner, wherein the first specific binding partner recognizes sialic acid, polysialic acid, or α-(2-8)-linked n-acetylneuraminic acid;*

*b) incubating NCAM bound to the first specific binding partner with a second specific binding partner, wherein the second specific binding partner recognizes an antigen selected from the group consisting of SCLC cell line antigens having a molecular weight of 170±10 kDa, 140±10 KDa, 105±10 KDa, 67±10 KDa, 50±10 KDa, and SCLC patient serum antigens having a molecular weight of 75±5 KDa, 105±15 KDa, 240±20 kDa; and*

*c) determining the amount of NCAM bound both to the first specific binding partner and to the second specific binding partner.*

*8. The method of claim 7, wherein the second specific binding partner recognizes a protein epitope on NCAM.*

*9. The method of claim 8, wherein the second specific binding partner is a an antibody or a receptor.*

*10. The method of claim 9, wherein the second specific binding partner is an antibody.*

*11. The method of claim 10, wherein the antibody is MAb BW SCLC-1.*

*12. The method of claim 10, wherein the antibody if MAb BW SCLC-2.*

*13. The method of claim 8, wherein the first specific binding partner is an antibody, a lectin, or a receptor.*

*14. The method of claim 13, wherein the first specific binding partner is an antibody.*

*15. The method of claim 14, wherein the first antibody is MAb 735.*

*16. The method of claim 8, wherein the first specific binding partner is bound to a solid phase.*

*17. The method of claim 8, wherein the first specific binding partner is bound to a label.*

*18. The method of claim 17, wherein the label is an enzyme, a luminophore, a fluorophore, a radioactive isotope, a colored particle, or an uncolored particle.*

*19. A heterogeneous or homogeneous method for the detection and determination of NCAM recognized by MAb BW SCLC-1, comprising the steps of:*

*a) incubating a sample of body fluid with a first specific binding partner, wherein the first specific binding partner recognizes sialic acid, polysialic acid, or α-(2-8)-linked n-acetylneuraminic acid;*

*b) incubating NCAM bound to the first specific binding partner with a second specific binding partner, wherein the second specific binding partner is MAb BW SCLC-1 or MAb BW SCLC-2; and*

*c) determining the amount of NCAM bound to the first specific binding partner and to the second specific binding partner.*

* * * * *

UNITED STATES PATENT AND TRADEMARK OFFICE

CERTIFICATE OF CORRECTION

PATENT NO. : RE 37,596 E
DATED : March 19, 2002
INVENTOR(S) : Bosslet et al.

It is certified that error appears in the above-identified patent and that said Letters Patent is hereby corrected as shown below:

Column 9,
Line 35, "claims 2, 3 or 4" should read -- claims 2, 3, and 4 --.

Column 10,
Line 17, before "an antibody", delete "a".
Line 22, "*if MAb*" should read -- *is MAb* --.

Signed and Sealed this

Sixth Day of May, 2003

JAMES E. ROGAN
*Director of the United States Patent and Trademark Office*